United States Patent
Bellon

(10) Patent No.: US 6,231,736 B1
(45) Date of Patent: May 15, 2001

(54) DETECTION OF ALCALINE ISOPHOSPHATASES BY ELECTROPHORESIS

(75) Inventor: Franck Bellon, Longjumeau (FR)

(73) Assignee: Sebia (FR)

( * ) Notice: Subject to any disclaimer, the term of this patent is extended or adjusted under 35 U.S.C. 154(b) by 0 days.

(21) Appl. No.: 09/597,382

(22) Filed: Jun. 19, 2000

(30) Foreign Application Priority Data

Mar. 10, 2000 (FR) .................................................. 00 03142

(51) Int. Cl.[7] ........................ B01D 57/02; B01D 59/42; C02F 1/469; C02F 1/26; C08F 2/58
(52) U.S. Cl. ........................ 204/450; 204/456; 204/466; 204/469; 204/546
(58) Field of Search ................................... 435/40, 287.2; 204/182.8, 456, 466, 467, 469, 546, 450; 436/501; 530/350

(56) References Cited

U.S. PATENT DOCUMENTS

| | | | |
|---|---|---|---|
| 4,681,842 | 7/1987 | Rosalki ................................... | 435/21 |
| 5,264,098 | 11/1993 | Chevigne ........................... | 204/182.8 |
| 5,667,654 | 9/1997 | Gombocz et al. ................... | 204/458 |
| 5,853,668 | 12/1998 | Begg et al. ........................ | 422/82.02 |

FOREIGN PATENT DOCUMENTS

| | | |
|---|---|---|
| B1 0 131 606 | 11/1986 | (EP) . |
| 0 493 996 A1 | 12/1991 | (EP) . |
| 0 848 251 | 6/1998 | (EP) . |
| WO 99 45374 | 9/1999 | (WO) . |

OTHER PUBLICATIONS

Schrelber et al., Alkaline phosphatases isoenzymes resolved by electrophoresis on lectin–containing agarose gel . Clin. Chem. 32, 1570–1573, Aug. 1986.*

Saward et al., Evaluation of two new methods for routine measurement of alkaline phosphatase isoenzymes J. Clin. Pathol. 45, 68–71, Jan. 1992.*

Sidney B. Rosalki, A. Ying Foo, Clinical Chemistry, 30/7, p. 1182–86 (1984) "Two methods for separating and quantifying bone and liver alkaline phosphatase isoezyme in plasma."

Van Hoof V.O., De Broe Marc E., Clinical Laboratory Sciences, vol. 31, issue 3 pp. 197–293 (1994) "Interpretation and clinical significance of alkaline phosphatase isoenzyme patterns."

Van Hoof V. Journal of Chromatography, vol. 646, pp. 235–43 (1993) "Comparison of two commercially available systems for the electrophoretic separation of alkaline phosphatase isoenzymes".

* cited by examiner

Primary Examiner—W. Gary Jones
Assistant Examiner—Frank Lu
(74) Attorney, Agent, or Firm—Lerner, David, Littenberg, Krumholz & Mentlik, LLP

(57) ABSTRACT

The invention concerns a process for separating alkaline phosphatase (ALP) isoenzymes from a biological sample by electrophoresis, characterized in that the electrophoresis is carried out on an electrophoresis support after depositing a solution of lectin onto the electrophoresis support in a predetermined localized zone, under conditions which permit interaction between said lectin and the ALP isoenzymes contained in the analyzed biological sample, deposition of the lectin solution further being carried out under conditions which are suitable to allow separation of the ALP isoenzymes constituted by the osseous fraction and by the hepatic fraction.

25 Claims, No Drawings

DETECTION OF ALCALINE ISOPHOSPHATASES BY ELECTROPHORESIS

BACKGROUND OF THE INVENTION

Alkaline phosphatase (EC 3.1.3.1.) (abbreviation:ALP) is a metalloenzyme consisting of a group of isoenzymes present in different tissues of animal organisms and in particular in man.

Alkaline phosphatase isoenzymes are important in protocols for diagnosing different conditions in adults or in children, and a number of methods have been proposed for separating and assaying such isoenzymes. ALP isoenzymes can be divided into four classes: non-specific tissue (bone, liver and kidney), adult intestinal, foetal intestinal, and placental. A number of variations can exist within a single class, namely:

hepatic: hepatic 1 (H1), hepatic 2 (H2);
ultrafast (UF);
osseous (Os);
placental: placental 1 (P1), placental 2 (P2);
intestinal: intestinal 1 (I1), intestinal 2 (I2), intestinal 3 (I3).

Thus nine principal fractions can be distinguished which have to be separated, identified and quantified in particular for their detection into hepatic and biliary disorders and into certain bone diseases, including osseous tumours or Paget's disease.

Reference will occasionally be made below to the term "fraction" to designate a class of ALP isoenzymes or a particular variant within a class of isoenzymes. On the electrophoresis support, a "fraction" corresponds to a band revealed after migration.

The most frequent routine analysis carried out on alkaline phosphatase isoenzymes consists of measuring the total enzymatic activity using a substrate of this enzyme, generally para-nitrophenylphosphate. That method, however, cannot determine the levels of the different isoenzymes.

The principal method for separative analysis of such compounds uses electrophoretic techniques. Isoelectrofocussing is occasionally used and can separate 10 to 20 bands depending on the procedure used. Identifying all of the bands is difficult, rendering clinical interpretation extremely awkward.

Zone electrophoresis enables a good separation of the principal forms of the isophosphatases. However, certain fractions are superimposed, in particular the Os, H1 and P1 fractions, and thus complementary treatments have to be carried out to separate and identify them. Such treatments must be carried out on the biological test samples to be tested before depositing them onto the gel.

Such treatments consist, for example, of thermal denaturing, incubation with specific inhibitors such as urea, amino acids, etc., enzymatic incubation with neuraminidase, ficin, phospholipase C, incubation with specific antiplacental or anti-intestinal antisera.

Several separation procedures which are in current use have been dealt with by Van Hoof V. O., De Broe Marc, E., Clinical Laboratory Sciences, vol. 31, issue 3 1994, "Interpretation and clinical significance of alkaline phosphatase isoenzyme patterns".

One particular procedure has been proposed in U.S. Pat. No. 5,264,098 which describes the separation of ALP isoenzymes using a gel electrophoresis reaction employing a gel buffer containing at least one non ionic detergent and an anionic detergent.

Available treatments for identifying and quantifying ALP isoenzymes have certain disadvantages as regards routine analysis. In addition to high costs, they can on the one hand be long and can considerably complicate manipulation, and on the other hand, complete determination (of all of the isoenzymes) necessitates a plurality of treatments (2 or 3) for a single sample, limiting the number of samples which can be simultaneously analysed on the one gel.

Other treatments have been proposed which, for example, recommend treating the sample prior to loading onto the electrophoresis gel. In this regards, the action of the WGA lectin (wheat germ agglutinin) is particularly interesting (see Sidney B. Rosalki, A. Ying Foo, Clinical Chemistry, 30/7, p. 1182–1186, 1984, "Two methods for separating and quantifying bone and liver alkaline phosphatase isoenzyme in plasma", European patent EP-A-0 131 606 dated May 11, 1986). EP-A-0 131 606 describes the differential detection of bone and liver ALP isoenzyme comprising treating the test sample with lectin, then incubating the mixture obtained followed by separating the ALP bound to the lectin from the fraction containing free ALP and determining the ALP activity in one of the two media or in both. In a particular implementation of that patent, the two fractions (ALP bound to lectin and free ALP) are separated by electrophoresis.

With the exception of the intestinal forms, all isophosphatases possess sialic acids and are thus affected by a treatment with WGA lectin to a greater or lesser extent. The osseous fraction is the most sialated and thus is affected the most by this treatment, which under suitable conditions retards its mobility and thus causes it to precipitate in a zone which is distinct from the zone where the hepatic fraction is located.

In order to render ALP isoenzyme precipitation more selective towards the osseous isoenzyme, certain authors have used detergents such as Triton X100 (Rosalki). However, despite the presence of such detergents, residual interactions of the WGA lectin with other isophosphatases subsist, which cause co-precipitation of such fractions with the osseous fraction.

In addition to this lack of specificity, a further disadvantage of this technique is to render the analysis considerably more complicated.

The publication by Rosalki S. B. et al, cited above, alternatively proposes incorporating lectin into the buffer used to impregnate the electrophoresis gel prior to using this gel. This dispenses with prior treatment of the sample. In that case, the majority of the osseous fraction is precipitated close to where the sample has been loaded. The mobility of all of the other isoenzymes with the exception of intestinal isoenzymes is affected by the action of the WGA lectin despite the presence of the detergents mentioned above.

In the context of that treatment, the properties of the lectin used are its ability to interact specifically with the ALP isoenzymes which contain sialic acids.

SUMMARY OF THE INVENTION

The present invention proposes means for at least partially overcoming the disadvantages stated in prior art methods. In particular, the invention defines a method enabling separation and identification of ALP isoenzymes which is improved as regards specificity and sensitivity.

The present invention also provides consumers, in particular clinicians, with a process for separating, identifying and quantifying the principal alkaline isophosphatases, which process can be carried out in a single step on a single electrophoresis support which is easy to produce.

The invention thus proposes a novel process for separating and identifying ALP isoenzymes by electrophoresis, characterized in that the lectin is deposited on the electrophoresis support in a localised manner.

The lectin deposited in solution in a localised manner can diffuse into the support while remaining localised in a determined zone of this support during electrophoretic migration.

The deposit in question, located close to the zone where the sample is deposited, is distinguished from the uniform loading over an extended zone or over the whole of the electrophoresis support as described in the prior art.

The invention thus provides a process for separating alkaline phosphatase isoenzymes from a biological sample by electrophoresis, characterized in that the electrophoresis reaction is carried out on an electrophoresis support after depositing a solution of lectin onto the electrophoresis support in a given zone, under conditions which permit interaction between said lectin and the ALP isoenzymes contained in the analysed biological sample, deposition of the lectin solution further being carried out under conditions which are suitable to allow separation of the ALP isoenzymes constituted by the osseous fraction and by the hepatic fraction.

The interaction in question leads to the formation of a complex between the lectin and the ALP isoenzyme until equilibrium is obtained.

The process of the invention enables the osseous fraction of the ALP to be acted on in a manner which is more specific than on the other ALP fractions because of the reaction of this fraction with the lectin.

The biological sample analysed can be any biological sample which may contain ALP, in particular a biological fluid sample such as a serum or plasma sample, or possibly a tissue sample removed from a patient.

In the invention, electrophoresis is carried out on any suitable electrophoresis support, in particular on a gel, more particularly on an agarose or a polyacrylamide gel, or on a porous membrane, in particular made of cellulose acetate.

The particular conditions defined above for carrying out the electrophoresis of the invention can be applied in the context of known electrophoresis methods which may or may not be automated.

The localised lectin deposit zone is determined as a function of the direction of migration of the sample and the lectin. Thus the lectin deposit zone is selected such that, during migration, the sample traverses the lectin, the mobility of the latter during migration having been taken into consideration. Similarly, the final position normally reached by the other ALP isoenzymes is taken into consideration in order to determine the lectin deposit zone with respect to that of the sample. In practice, the lectin and the sample are 1 to 10 mm apart, advantageously 5 mm, when the sample is loaded.

The other conditions for localised depositing of the lectin, such as the concentration of the lectin, the time for application to the electrophoresis support, are determined such that they enable osseous and hepatic ALP isoenzymes to be separated during electrophoresis under the migration reaction conditions.

In other words, once the parameters of electrophoresis have been determined particularly as regards depositing the lectin, the process of the invention can separate the osseous and hepatic isoenzymes under conditions which are satisfactory for identifying them with respect to the other ALP isoenzymes, and preferably to quantify them. The mobility of the other ALP isoenzymes, affected during passage through the zone where the lectin is present, returns to normal outside this zone.

Since the osseous ALP fraction is more sialated, its electrophoretic migration is the most affected by the passage of the sample through the lectin deposited on the support. As a result it is precipitated in a zone which may be distinguished from the migration zone of other ALP isoenzymes.

DESCRIPTION OF THE PREFERRED EMBODIMENTS

In a preferred embodiment of the invention, a process for separating alkaline phosphatase (ALP) isoenzymes by electrophoresis is characterized in that it comprises:

depositing the biological sample containing the ALP isoenzymes to be separated on the electrophoresis support;

depositing a lectin solution which can interact with the ALP isoenzymes contained in the sample on the electrophoresis support;

applying an electric field to permit electrophoretic separation by migration of the ALP isoenzymes under conditions which can permit differential separation of the osseous and hepatic ALP fractions;

revealing the separated ALP isoenzymes.

Revealing is carried out using any known means, preferably using an ALP substrate.

At the end of the steps resulting in separation of the ALP isoenzymes on the electrophoresis support, a quantitative analysis of the different separated isoenzymes, or certain of them, can be carried out.

Different methods can be used to quantify the ALP isoenzymes detected at the end of electrophoresis. As an example, the densitometry of the electrophoresis support can be measured after staining the separated ALP fractions using an ALP substrate.

When the osseous ALP fraction is in excess with respect to the fixing capacity of the lectin deposited on the gel, the lectin may not precipitate the whole of this fraction. In this case, the non precipitated portion continues to migrate with the other fractions, and can be found in the form of a smear close to the subjacent isoenzymes, in particular H2, I1, I2 and I3. In this case, the different isoenzymes can be quantified by depositing the same sample a second time on the same support, in the absence of lectin. On the "no lectin" pattern, the percentages of the H1 Os P1 block and the separated fractions H2, I1, P2, I2, I3 and UF are determined. The percentage of the Os fraction is obtained by deducting the percentages of H1 and P1 determined from the "with lectin" profile from the H1 Os P1 block.

Within the context of the definitions given above, when carrying out electrophoresis in the presence of a localised deposit of lectin on the electrophoresis support, the lectin and the sample can be deposited simultaneously on the electrophoresis support.

In another embodiment of the invention, the sample and the lectin are deposited at different times.

Further, the sample and the lectin solution can respectively be deposited on the electrophoresis support over periods which may be identical or different.

Advantageously, within the context of the definitions given above, if necessary taken in combination, the lectin and the sample are deposited over a substantially identical period of time, and preferably simultaneously for practical and economic reasons.

For a given sample and a determined concentration of lectin in the solution, the sample application and lectin application period, and thus the quantity of sample and lectin deposited on the electrophoresis support, is selected so as to precipitate the Os fraction of the ALP isoenzymes such that the osseous and hepatic fractions are separated during migration. To determine the concentration of the lectin solution and the period over which the solution is applied to the electrophoresis support, the temperature reached by the support during migration is also taken into account.

Indeed, since the interaction of the lectin with the osseous ALP fraction is dependent on temperature, the temperature of the electrophoresis support during the migration step must be taken into account. A reduction in the lectin-osseous ALP interaction due to an increase in the temperature of the electrophoresis support can be compensated for by an increase in the quantity of lectin deposited, for example by increasing the concentration of the lectin solution used.

These parameters can be determined in the light of the indications below and the values given in the examples and can if necessary be adapted to the selected electrophoresis conditions, by carrying out tests such as those which are given in the examples below.

The sample application and/or lectin solution application period can vary and can in particular be in the range of 5 to 20 min, preferably 15 minutes, for the sample and/or for the lectin.

Depositing can be carried out using any known manual or automated means, for example using "comb" type applicators, for example the devices described in European patent application EP-A-0 493 996.

The lectin used is in the form of an aqueous solution.

Thus the concentration of lectin deposited on the electrophoresis support used under normal conditions is in the range of 0.1 mg/ml to the limit of solubility of lectin in water. This concentration is advantageously in the range of 0.5 to 15 mg/ml, preferably in the range of 1 to 10 mg/ml.

In a particular implementation of the invention, the process is characterized in that when the lectin concentration is in the range of 1 to 10 mg/ml, the migration temperature is respectively in the range of 18° C. to 53° C. These conditions are applicable inter alia to depositing a lectin solution over a period of close to about 15 minutes with a comb type applicator as described in European patent application EP-A-0 493 996.

The invention particularly concerns an implementation of an electrophoresis process in which, when the ALP isoenzymes present in the test sample have an electrophoretic mobility in the direction of the anode, the lectin is deposited between the anode and the sample deposit zone.

Advantageously in this case, the lectin is deposited between the biological sample deposit point and the zone normally occupied by intestinal fraction 3 (I3) at the end of the migration step, when this fraction is present in the sample.

Different lectins can be used in the invention. Lectins are proteins which fix sialated groups. Lectins which can be used in the present invention which can be cited include wheat germ (Triticum vulgaris) lectin, or WGA (Wheat Germ Agglutinin). WGA lectin can be obtained from Sigma, Pharmacia, etc.

The invention also concerns a process satisfying the definitions given above, taken separately or in combination, in which separation of fractions other than the osseous and hepatic 1 of ALP is improved.

The invention thus makes available, under conditions which are compatible with routine laboratory analyses, means for in vitro detection in a biological sample of the abnormal presence of one or more ALP isoenzymes.

This process can in particular be carried out during a protocol for diagnosing a hepatic or biliary disorder corresponding to the abnormal presence of the hepatic ALP fraction. The invention can also enable the abnormal presence of the osseous fraction to be researched in the context of the diagnosis of osseous disorders.

The invention also concerns kits for carrying out separation of fractions constituted by ALP isoenzymes by electrophoresis.

The process of the invention thus has the advantage of using a single electrophoresis support, without prior treatment of the sample, to carry out qualitative determination of all of the ALP isoenzymes in one deposit and their quantitative determination in two deposits onto a single support. The electrophoresis support is free of lectin prior to its use, which enables it to be stored under the usual temperature conditions and does not change its manufacturing cost.

A kit comprises, for example:
  an electrophoresis support comprising a porous material suitable for depositing a biological sample to be analysed and for carrying out electrophoretic migration;
  a solution of lectin in a concentration in the range of 0.1 mg/ml to 15 mg/ml, advantageously in the range of 1 to 10 mg/ml, preferably in the range of 1 to 10 mg/ml.

The kit of the invention can also comprise the buffer or buffers required for the electrophoresis reaction. It can also contain ALP activity revealing reagents.

Further advantages and features of the invention will become more clear from the following examples.

EXAMPLES

Principles of the Reaction Using Lectin When it is Uniformly Distributed in the Electrophoresis Gel The interaction of the WGA lectin with a slightly sialated isophosphatase can be represented by the equilibrium:

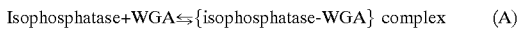

$$\text{Isophosphatase} + \text{WGA} \rightleftharpoons \{\text{isophosphatase-WGA}\} \text{ complex} \qquad (A)$$

Under normal electrophoresis conditions, namely at a basic pH, isophosphatases have an anodic mobility while lectin has a slightly cathodic mobility. The anodic mobility of the {isophosphatase-WGA} complex will thus be lower than that of free isophosphatase.

During the whole of the migration period, the isophosphatase will interact with the WGA lectin in accordance with the equilibrium of reaction (A) and thus will be slowed down.

Thus the pattern obtained on the gel with no WGA lectin where, under the given conditions, all fractions are separated with the exception of the block constituted by the H1, Os (possibly P1) isoenzymes, will lead, for a gel incorporating WGA lectin over its entire surface, to a pattern where the H1 (possibly P1) will be disengaged from the osseous but where the HI, P1 fractions on the one hand and the H2, I2 fractions on the other hand, which are resolved on the gel without WGA lectin, will be merged. It would then be necessary, even for a simple qualitative estimation of the isoenzymes of a sample, to carry out electrophoresis on two types of gel, which would therefore complicate the analysis.

In addition to this disadvantage, WGA lectin is heat sensitive which renders the production of gels containing it very difficult; further, consumers are obliged to store these gels between 40° C. and 80° C. to preserve their performance intact.

Principles of the Reaction of the Invention, Using Lectin Deposited Onto the Electrophoresis Gel in a Localised Manner In the invention, a solution of WGA lectin is deposited in front of the sample, i.e., between the sample and the anode. The electrophoresis gel is thus not impregnated with lectin over its entire surface. The WGA lectin may or may not be deposited simultaneously with the sample. Once both deposits have been carried out, the voltage is applied to obtain electrophoretic separation.

Under these conditions, the major portion of the Os fraction precipitates out when it goes through the zone where the WGA lectin has been deposited. The electrophoretic mobility of the other isophosphatase fractions is affected by the WGA lectin in accordance with the equilibrium of the reaction:

Isophosphatase+WGA⇆{isophosphatase-WGA} complex, but only when traversing the zone containing the WGA lectin. This zone is very reduced in size (<1 mm) which means that the profile remains practically identical to that obtained in the absence of lectin, with the exception of the osseous fraction which is disengaged from the H1 and P1 fractions. Under these conditions, electrophoresis of the sample with the deposited lectin in front of the sample permits qualitative analysis on a single gel in a single step: all of the isoenzymes can be identified from their position and without the need for complementary treatments to be carried out on the sample.

In the case when the different isoenzymes which have been separated and revealed by a suitable reagent have to be quantified, account must be taken of the fact that precipitation of the osseous fraction by the WGA lectin is not complete, in particular in the case where this osseous fraction is highly increased. A portion of the osseous alkaline phosphatase molecules escape precipitation when going through the lectin deposit. The Os-WGA bond is, however, sufficient for these non-precipitated osseous alkaline phosphatase molecules to entrain WGA lectin with them. They are thus sufficiently slowed so that they do not reach the H1P1 zone. Thus in addition to the precipitation curve of the osseous fraction, a smear of osseous alkaline phosphatase is obtained which reaches to the zone to which the H2 migrates. Under these conditions, quantification of the isoenzymes subjacent to this streak, namely the isoenzymes H2, I1, I2, I3, is disturbed by this smear.

To enable quantification in a situation where the quantity of the Os fraction risks being higher than that which can precipitate, two deposits of the same sample should be made side by side, one with the lectin deposit, the other without. The H1 and P1 fractions can be quantified on the pattern with the WGA lectin. The percentages of the Hi Os P1 block and the separated H2, I1, P2, I2, I3 and UF fractions are determined using the pattern with no lectin. The percentage of the Os fraction is obtained by subtracting the H1 and P1 percentages determined using the profile with lectin from the H1 Os P1 block.

Thus a single gel can be used to determine, in a single step with two loads, the percentage of all of the isoenzymes with no prior treatment of the sample.

Concentration of Lectin and Temperature of Electrophoresis.

The concentration of lectin to be used and the migration temperature (temperature of the electrophoresis support) are closely linked. The equilibrium for formation of the isophosphatase-WGA lectin complex is indeed temperature-dependent. Thus increasing the temperature encourages dissociation of the complex. The lectin concentration must be increased to obtain the same precipitating power of the osseous fraction.

In practice, the concentration of the lectin to be used is a function of the gel and can be selected using the following table:

| Temperature of gel during migration ° C. | Concentration of lectin, mg/ml |
|---|---|
| 18 | 1 |
| 28 | 2 |
| 38 | 3 |
| 48 | 5 |
| 53 | 10 |

Thus if the process is carried out in accordance with the invention with an electrophoresis system which cannot control the migration temperature (Example 1), the lectin concentration has to be increased to take account of the maximum temperature achieved in the gel during migration. This temperature depends on a number of parameters such as the ionic strength and the dimensions of the gel, the migration parameters and the external temperature during migration. Under the conditions used in Example 1, the maximum temperature reached by the gel is close to 38° C., and thus a lectin concentration of 3 mg/ml is used. In Example 2, the instrument can regulate the electrophoresis temperature at 20° C. However, when the electrophoresis is carried out at a constant power of 20 W, the effective temperature of the gel is 28° C. As a result, the concentration of lectin necessary to obtain the desired effect is 2 mg/ml.

Position and Duration of Lectin Depositing

Under the pH conditions (basic) used for electrophoresis, the mobility of all of the alkaline isophosphatases is in the anode direction; in contrast, lectin has a very slight mobility in the cathode direction. In order for the osseous fraction to encounter the lectin, the lectin has to be deposited between the sample and the anode. More precisely, it must be deposited at a distance which is less than or equal to that traversed by the osseous fraction under the migration conditions used and in the absence of lectin. However, in order to prevent precipitation of the osseous fraction in a zone already occupied by other fractions, it appears more judicious to deposit the lectin at a distance between the sample and the position which the I3 fraction occupies at the end of migration. In practice, the lectin is deposited in front of the sample at a distance in the range of 1 to 10 mm, preferably close to 5 mm.

The lectin is deposited at the same time or after the sample. The two do not have to be deposited simultaneously. However, if the sample and the lectin are not deposited at the same time, care must be taken to prevent diffusion of the first deposit when depositing the second. For this reason it is easier to deposit the sample and the lectin simultaneously and over the same period. Further, the two deposits are parallel to each other and perpendicular to the direction of migration.

Example n° 1

Gel with the following composition:

| Agarose | 1% |
|---|---|
| Tris | 0.03 M |
| Sodium Barbital | 0.025 M |
| Barbital acid | 0.005 M |
| Sodium azide | 1 g/l |
| Triton X 100 | 10 g/l |
| Nonidet NP 40 | 5 g/l |

40 ml of demineralised water and 0.5 g of agarose were introduced into a 100 ml Erlenmeyer flask. After boiling for 5 minutes with constant stirring, the agarose had dissolved to produce a perfectly clear solution. The temperature of this solution was reduced to 50° C. in a thermostated bath. 10 ml of a concentrated buffer solution containing 18 g/l of Tris, 27.75 g/l of sodium Barbital, 4.6 g/l of Barbital acid, 5 g/l of sodium azide, 50 g/l of Triton X 100 and 25 g/l of Nonidet NP 40 were introduced into a 50 ml Erlenmeyer flask. This solution was maintained at 50° C. in the thermostatted bath.

The pre-heated buffer was added to the agarose solution. It was homogenised and maintained at 50° C.

5 ml of the above solution, removed with a pipette, was then uniformly poured onto a 10×8 cm hydrophilic plastic sheet.

After gelling and stabilisation, the gel could be used. Fresh sera to be analysed were deposited in 2 adjacent deposits, 2.5 cm from the edge, on the cathode side. A 3 mg/ml solution of Wheat Germ Agglutinin (WGA) lectin was applied simultaneously and over the same period 32 mm in front of one of the 2 deposits of each sample, i.e., between the sample and the anode. The application time could be 15 minutes for each deposit made with a microporous membrane applicator as sold by Sebia, described in European patent application EP-A-0 493 996.

The alkaline isophosphatases were separated by electrophoresis in a vessel the tanks of which contained a Tris 0.003 M, sodium Barbital 0.025 M, Barbital acid 0.005 M, sodium azide 0.1 g/l buffer for a period of 50 minutes at a constant voltage of 100 V.

Incubating the gel with a conventional substrate for this enzyme (for example bromochloroindolyl phosphate and nitrobluetetrazolium) then revealed the alkaline phosphatase activities. A blue stain was thus obtained at the location of each isophosphatase fraction, proportional to its activity. After revealing, the gel was washed then dried and analysed by densitometry to quantify the different alkaline isophosphatases.

Example n° 2

Gel with the following composition:

| Agarose | 1% |
|---|---|
| Tris | 0.38 M |
| Boric acid | 0.06 M |
| sodium azide | 1 g/l |
| Triton X 100 | 10 g/l |
| Nonidet NP 40 | 5 g/l |

40 ml of demineralised water and 0.5 g of agarose were introduced into a 100 ml Erlenmeyer flask. After boiling for 5 minutes with constant stirring, the agarose had dissolved to produce a perfectly clear solution. The temperature of this solution was reduced to 50° C. in a thermostatted bath. 10 ml of a concentrated buffer solution containing 229.9 g/l of Tris, 18.55 g/l of boric acid, 5 g9l of sodium azide, 50 g/l of Triton X 100 and 25 g/l of Nonidet NP 40 were introduced into a 50 ml Erlenmeyer flask. This solution was maintained at 50° C. in the thermostatted bath.

The pre-heated buffer was added to the agarose solution. It was homogenised and maintained at 50° C.

5 ml of the above solution, removed with a pipette, was then uniformly poured onto a 10×8 cm hydrophilic plastic sheet.

After gelling and stabilisation, the gel could be used. Fresh sera to be analysed were deposited in 2 adjacent deposits, 2.5 cm from the edge, on the cathode side. A 2 mg/ml solution of Wheat Germ Agglutinin (WGA) lectin was applied simultaneously and over the same period 5 mm in front of one of the 2 deposits of each sample, i.e., between the sample and the anode.

The alkaline isophosphatases were separated by electrophoresis in an apparatus which could adjust the temperature to 20° C. Migration was carried out at a constant power of 20 W for 20 minutes.

The alkaline phosphatase activities and densitometry were measured as in the previous example.

What is claimed is:

1. An electrophoretic process for separating alkaline phosphatase isoenzymes from a biological sample comprising the steps of: depositing a solution of lectin onto an electrophoresis support in a first localised zone, and depositing a biological sample including alkaline phosphatase isoenzymes onto said electrophoresis support in a second localised zone which is spaced apart from said first localized zone and applying an electric field to said electrophoresis support to permit electrophoretic separation by migration of said isozymes from said second localized zone such that at least one of said isozymes migrates through said first localized zone.

2. The process for separating alkaline phosphatase isoenzymes of claim 1, further comprising the step of quantitative analysis of at least one of said isoenzymes following said separation.

3. The process for separating alkaline phosphatase isoenzymes of claim 1, wherein said lectin solution and said biological sample are each deposited over a period of between about 5 to 20 minutes.

4. The process for separating alkaline phosphatase isoenzymes of claim 1, wherein the concentration of said lectin solution deposited is determined based upon the migration temperature and the period over which said lectin solution is applied to said support.

5. The process for separating alkaline phosphatase isoenzymes of claim 4, wherein said concentration of said lectin solution ranges from between about 0.1 mg/ml to the limit of solubility lectin in water.

6. The process for separating alkaline phosphatase isoenzymes of claim 5, wherein said concentration of said lectin solution ranges from between about 1 to 10 mg/ml.

7. The process for separating alkaline phosphatase isoenzymes of claim 4, wherein said migration temperature ranges from between 18° C. to 53° C.

8. The process for separating alkaline phosphatase isoenzymes claim 4, wherein said concentration of said lectin solution is determined as a function of the maximum migration temperature achieved in the electrophoresis support during said migration.

9. The process for separating alkaline phosphatase isoenzymes of claim 1, wherein said electric field is applied between an anode and a cathode and wherein said isozymes migrate toward said anode under the influence of said electric filed and wherein said first localized zone is located between said anode and said second localised zone.

10. The process for separating alkaline phosphatase isoenzymes of claim 1, wherein said lectin is deposited between the biological sample and a position normally occupied by an intestinal fraction 3 (I3) at the end of said migration step.

11. The process for separating alkaline phosphatase isoenzymes of claim 1, wherein the lectin is wheat germ lectin.

12. The process for separating alkaline phosphatase isoenzymes of claim 1, wherein said electrophoresis support is an agarose gel or polyacrylamide.

13. The process for separating alkaline phosphatase isoenzymes of claim 1, wherein said electrophoresis support is a cellulose acetate membrane.

14. The process for separating alkaline phosphatase isoenzymes of claim 2, wherein said quantitative analysis is carried out by measuring the densitometry of said electrophoresis support after staining.

15. The process for separating alkaline phosphatase isoenzymes of claim 1 wherein said alkaline phosphatase isoenzymes includes a osseous fraction, at least a potion of which does not migrate through said first localized zone.

16. The process for separating alkaline phosphatase isoenzymes of claim 15 wherein said alkaline phosphatase isoenzymes includes at least one hepatic fraction, which does migrate through said first localised zone thereby producing separation between said osseous and hepatic fractions.

17. The process for separating alkaline phosphatase isoenzymes of claim 2 wherein said alkaline phosphatase isoenzymes includes a osseous fraction, at least a potion of which does not migrate through said first localized zone.

18. The process for separating alkaline phosphatase isoenzymes of claim 17 wherein said alkaline phosphatase isoenzymes includes at least one hepatic fraction, which does migrate through said first localised zone thereby producing separation between said osseous and hepatic fractions.

19. The process for separating alkaline phosphatase isoenzymes of claim 2 wherein the separated ALP isoenzymes are quantitatively analyzed.

20. The process for separating alkaline phosphatase isoenzymes of claim 19, wherein said quantitative analysis is carried out by measuring the densitometry of said electrophoresis support after staining.

21. The process for separating alkaline phosphatase isoenzymes of claim 1, wherein said concentration of said lectin solution ranges from between about 0.1 mg/ml to the limit of solubility lectin in water.

22. The process for separating alkaline phosphatase isoenzymes of claim 2, wherein said lectin is deposited between the biological sample and a position normally occupied by an intestinal fraction 3 (I3) at the end of said migration step.

23. An electrophoretic process for detecting the presence of at least one alkaline phosphatase isoenzyme in a biological sample deposited on an electrophoretic support, comprising the steps of: depositing a solution of lectin onto said electrophoresis support in a first localised zone, depositing a biological sample including at least one alkaline phosphatase isoenzyme onto said electrophoresis support in a second localised zone which is spaced apart from said first localised zone such that at least one alkaline phosphatase isoenzyme contained within said biological sample will interact with said lectin as it migrates toward an electrode upon the application of an electric field to said electrophoresis support.

24. The process of claim 23 further comprising the step of correlating the presence of said at least one alkaline phosphate isoenzyme with a hepatic or bilary disorder.

25. The process of claim 23 further comprising the step of correlating the presence of said at least one alkaline phosphate isoenzyme with an osseous disorder.

* * * * *

UNITED STATES PATENT AND TRADEMARK OFFICE
CERTIFICATE OF CORRECTION

PATENT NO.     : 6,231,736 B1
DATED          : May 15, 2001
INVENTOR(S)    : Franck Bellon It is certified that error appears in the above-identified patent and that said Letters Patent is hereby corrected as shown below:

Column 6,
Line 66, "between 40° C. and 80° C. to" should read -- between 4° C. and 8° C. to --.

Column 10,
Line 4, "5g9l of sodium azide," should read -- 5 g/l of sodium azide, --.
Line 64, "zymes claim 4," should read -- zymes of claim 4 --.

Column 11,
Line 5, "electric filed and" should read -- electric field and --.
Line 25, "zymes includes" should read -- zymes include --.
Line 29, "zymes includes" should read -- zymes include --.
Line 34, "zymes includes" should read -- zymes include --.
Line 38, "zymes includes" should read -- zymes include --.

Column 12,
Line 22, "localised zone, depositing" should read -- localised zone; depositing --.

Signed and Sealed this

Thirteenth Day of November, 2001

*Attest:*

NICHOLAS P. GODICI
*Attesting Officer*    Acting Director of the United States Patent and Trademark Office